United States Patent [19]

Van Scott et al.

[11] 4,287,214

[45] Sep. 1, 1981

[54] DITHRANOL COMPOSITIONS STABILIZED WITH ALPHA HYDROXYACIDS

[76] Inventors: Eugene J. Van Scott, 1138 Sewell La., Rydal, Pa. 19046; Ruey J. Yu, 4 Lindenwold Ave., Ambler, Pa. 19002

[21] Appl. No.: 78,181

[22] Filed: Sep. 24, 1979

[51] Int. Cl.$^3$ ............................................. A61K 31/05
[52] U.S. Cl. .................................... 424/346; 424/279; 424/313; 424/317; 424/320; 424/365
[58] Field of Search ................................ 424/343, 346

[56] References Cited

U.S. PATENT DOCUMENTS 3,920,835  11/1975  Van Scott et al. .................. 424/311

OTHER PUBLICATIONS

Chemical Abstracts 78:75809q, (1973).
Sagarin–Cosmetics, Science & Technology, pp. 1066–1067, (1957).

Primary Examiner—Leonard Schenkman
Attorney, Agent, or Firm—LeBlanc, Nolan, Shur & Nies

[57] ABSTRACT

Chemically stable dithranol compositions useful as topical treatment for inflammatory disorders such as psoriasis, eczema and seborrheic dermatitis are disclosed. Incorporation of a certain alpha hydroxyacid as its free acid, lactone, amide or salt form in dithranol containing compositions has been found to chemically stabilize said compositions. The alpha hydroxyacids include glyceric acid, gluconic acid, galacturonic acid, glucuronic acid, glucoheptonic acid, galactonic acid, malic acid, mucic acid, citric acid, saccharic acid, tartaric acid, tartronic acid, isocitric acid and glucuronamide. A single member of the above alpha hydroxyacids may be present in a total amount of from 0.01 to 1 percent by weight of the total composition, or a plurality thereof may be present in a preferred concentration range of from 0.02 to 0.5 percent by weight of the total composition.

24 Claims, No Drawings

DITHRANOL COMPOSITIONS STABILIZED WITH ALPHA HYDROXYACIDS

Dithranol, also known as anthralin, is chemically identified as 1,8,9-anthracenetriol with a molecular weight of 226 ($C_{14}H_{10}O_3$). It is a yellowish brown, crystalline powder, odorless and tasteless. Dithranol is insoluble in water but slightly soluble in alcohol and ether. It is more soluble in chloroform and acetone. A dithranol 2 percent solution in acetone can be readily prepared at room temperature.

Dithranol is known to be effective topically in the treatment of psoriasis, chronic eczemas, dermatophytoses, alopecia areata and other skin disorders. It is normally applied in concentrations of from 0.1 to 1 percent in ointment or paste vehicles.

The topical use of dithranol, however, has been inhibited by three major problems, namely (a) instability, (b) irritation and (c) staining.

Dithranol in aqueous organic solution, lotion, gel or cream is rapidly oxidized in the presence of air to a brown-to-dark-purple product. The oxidized form of dithranol is therapeutically ineffective for topical treatment of many skin disorders.

Because of the chemical instability of dithranol in air and water the commercial product has necessarily been formulated in petrolatum ointment or zinc oxide paste and formulated to contain higher than needed concentrations of dithranol, ranging, normally, from 0.1 to 1 percent. Such high concentrations have a tendency to irritate or burn human skin when the composition is topically applied onto skin inflamed by psoriasis and eczema.

In addition, dithranol is chemically sensitive to alkali and air. Therefore, the therapeutic compositions containing high concentrations of dithranol often stain both the skin and clothing especially under the conditions when an alkaline soap or detergent is used to cleanse the skin or to launder clothing.

Many attempts have been made to stabilize the dithranol compositions for topical use. Such attempts include the addition of common reducing agent preservatives such as BHT (butylated hydroxytoluene), BHA (butylated hydroxyanisole), Vitamin C (ascorbic acid) and other chemicals such as salicylic acid.

We have however found that addition of BHT, BHA, Vitamin C or salicylic acid does not sufficiently prevent oxidation and discoloration of dithranol compositions.

We have also found that addition of strong reducing agents such as sodium bisulfite, sodium metabisulfite and stannous chloride will prevent air oxidation of dithranol compositions, but only for a few weeks. Such compounds will not stabilize therapeutic formulations for more extended periods of time.

In our prior patent, U.S. Pat. No. 3,879,537, entitled Treatment of Ichthyosiform Dermatoses, we described and claimed the use of certain alpha hydroxyacids, alpha ketoacids and related compounds for topical treatment of fish-scale like (ichthyotic) conditions in humans. In our U.S. Pat. No. 3,920,835, entitled Treatment of Disturbed Keratinization, we described and claimed the use of these certain alpha hydroxy-acids, alpha ketoacids and their derivatives for topical treatment of dandruff, acne, and palmar and plantar hyperkeratosis. In out patent application entitled Therapuetic Treatment of Dry Skin, Ser. No. 720,835, filed Sept. 7, 1976, now U.S. Pat. No. 4,105,783, we described and claimed the use of alpha or beta hydroxyacids or alpha ketoacids for topical treatment of dry skin, and in our patent application entitled Topical Treatment of Dry Skin, filed July 25, 1979, we described and claimed the use of these and related compounds in the topical treatment of dry skin. The disclosures of said patents and patent application are hereby incorporated by reference. In addition, we discovered certain of these compounds enhance the topical activity of certain corticosteroids. The use of these compounds as enhancing additives with corticosteroids was described and claimed in our patent application entitled Additives Enhancing Topical Corticosteroid Action, Ser. No. 65,332, filed Aug. 9, 1979, now U.S. Pat. No. 4,246,261, which disclosure is also hereby incorporated by reference.

It has now been discovered that certain alpha hydroxyacids when added to the dithranol compositions prevent the air oxidation of dithranol. The dithranol compositions thus stabilized with alpha hydroxyacids have been found to have an acceptable extended shelf life while retaining therapeutically efficacy for the topical treatment of psoriasis, eczema and seborrhea, and the like.

The alpha hydroxyacid stabilizng agents of this invention may be grouped in the following two classes.

The first class of alpha hydroxyacids is a glyceric acid derivative with the following chemical structure:

$$R(CR_1OH)_n COOH$$

$n = 2,3,,5,6$ or $7$ $R, R_1 = H, CHO, alkyl$ or aryl of 1 to 7 carbon atoms

The glyceric acid derivative may be present as a free acid, a lactone or an amide form. Representative glyceric acid derivatives which are effective in stabilizing dithranol compositions are listed below:

| 1. | Glyceric acid | 7. | Galactonolactone |
| 2. | Gluconic acid | 8. | Glucuronic acid |
| 3. | Gluconolactone | 9. | Glucuronolactone |
| 4. | Glucoheptonic acid | 10. | Galacturonic acid |
| 5. | Glucoheptonolactone | 11. | Galacturonolactone |
| 6. | Galactonic acid | 12. | Glucuronamide |

The second class of alpha hydroxyacids is alpha hydroxy polycarboxylic acid with the following chemical structure:

$$(CRX)_m (COOH)_n$$

$X = OH$ or $H$ when $m \geq 2$ and with one OH present
$m = 1,2,3,4,5,6$
$n = 2,3,4$
$R = H, CHO, alkyl$ or aryl of 1 to 7 carbon atoms The alpha hydroxy polycarboxylic acids may be present as a free acid, a lactone, an amide or a salt form. Representative alpha hydroxy polycarboxylic acids which are effective in stabilizing dithranol compositions are listed below:

| 1. | Tartronic acid | 9. | Mucic acid lactone |
| 2. | Malic acid | 10. | Saccharic acid monopotassium salt |
| 3. | Tartaric acid | 11. | Saccharic acid monosodium salt |
| 4. | Citric acid | 12. | Saccharic acid monoammonium salt |
| 5. | Isocitric acid | 13. | Tartaric acid monoamide |

| | -continued | | |
|---|---|---|---|
| 6. | Saccharic acid | 14. | Citric acid diamide |
| 7. | Mucic acid | 15. | Tartaric acid monoethyl ester |
| 8. | Saccharic acid lactone | 16. | Isocitric acid lactone |

While certain types of alpha hydroxyacids namely those with two or more than two hydroxy groups and a single carboxylic acid group or a single hydroxy group and two or more than two carboxylic acid groups are effective in stabilizing dithranol composition for topical treatment of psoriasis, other types of alpha hydroxyacids are not satisfactorily effective. For example, we have found that glycolic acid, lactic acid, 2-hydroxy isobutyric acid and mandelic acid were capable of stabilizing dithranol compositions only for a short period of time.

Effective alpha hydroxyacids of this invention may be present in dithranol compositions in several chemical forms: a free acid, a lactone, an amide, or a partial ester or salt of ammonium hydroxide or an organic or inorganic alkali. Certain forms are more effective, however, and are therefore preferred. The lactone form is as potent as the free acid form. The partial ester or salt form, however, is less effective than the free acid form. For example, D-saccharic acid monopotassium salt is less effective than D-saccharic acid. A fully neutralized salt form of an alpha hydroxyacid has also been found to be effective only in an acidic medium. For example, citric acid trisodium salt is effective when the composition pH is at or less than 5.0.

Stabilized dithranol compositions may be prepared in non-aqueous vehicles such as petrolatum or paste, or in oil-in-water emulsions such as hydrophilic ointment, U.S.P. or in water-in-oil emulsions of our inventions, entitled Stabilized Water-In-Oil Emulsions, U.S. patent application Ser. No. 43,266, filed May 29, 1979, and Stable Water-In-Oil Emulsions U.S. patent application Ser. No. 67,714 filed Aug. 17, 1979, now U.S. Pat. No. 4,252,796.

The dithranol compositions formulated in petrolatum or in zinc oxide paste exhibit a sticky or greasy feeling when topically applied to the skin. Although the dithranol compositions formulated in oil-in-water emulsions such as hydrophilic ointment, U.S.P. are less greasy on topical application to the human skin, the chemical stability and the therapeutic efficacy of dithranol are markedly compromised.

We have found that a preferred vehicle for a therapeutic agent useful in the topical treatment of inflammatory skin conditions is a water-in-oil emulsion as described in our above U.S. patent applications which are hereby incorporated by reference. The reasons are as follows:

Inflammatory skin diseases are clinically characterized by redness, swelling and heat, and may or may not be accompanied by an itching sensation or pain. In clinical treatment of most inflammatory skin disorders, including psoriasis, dermatitis and eczema, tests have shown that the most prompt relief and healing is obtained with the medicinal ingredient incorporated in a vehicle containing water which is applied to the skin, and the area affected covered with an occlusive dressing such as a plastic film. A vehicle then most useful in the treatment of such inflammatory skin diseases optimally has properties that (A) provide moisture and (B) provide occlusion.

Since an oil-in-water emulsion has water in the external phase and oil as a dispersion medium, use of this type of emulsion in treatment of inflammatory skin diseases provides only moisture but not occlusion. In contrast, petrolatum or its paste provides occlusion, but no moisture. A water-in-oil emulsion has oil in the external phase and water as a dispersion medium. Therefore, the water-in-oil emulsion which is water-non-washable provides both moisture and occlusion. We have previously shown that such an emulsion is more efficacious, using the same concentration of active ingredient than in petrolatum or in an oil-in-water emulsion such as hydrophilic ointment.

Accordingly, it is an object of this invention to provide dithranol compositions stabilized with alpha hydroxyacids for topical application to alleviate the symptoms of skin disorders in humans.

It is another object of this invention to provide certain classes of alpha hydroxyacids which can stabilize the dithranol composition useful for topical administration to alleviate the symptoms of skin diseases.

It is yet another object of this invention to provide a method for effectively stabilizing dithranol compositions for topical treatment of cutaneous diseases.

These and other objects will become readily apparent with reference to the following description.

PREPARATION OF THE THERAPEUTIC COMPOSITIONS

In a preferred method for preparing the stable dithranol compositions of this invention, at least one of the aforementioned alpha hydroxyacids is initially dissolved in water. The solution thus prepared is admixed with a water-in-oil emulsion vehicle. Dithranol is then dissolved in acetone or any other compatible organic solvent and the light yellowish solution thus formed is admixed with the above emulsion vehicle containing the alpha hydroxyacid stabilizing agent. The emulsion may be one of those disclosed in our above-identified patent applications.

The concentration of dithranol may range from 0.01 to 0.05 percent, by weight, to produce a therapeutic composition. The preferred concentration range, however, is from 0.01 to about 0.1 percent. As noted above, prior art formulations used much higher concentrations of up to 1 percent to overcome chemical instability.

The concentration of acetone or whatever organic solvent is used for dissolution of dithranol may range from 0.5 to 25 percent by volume of the total composition. The preferred concentration range, however, is from 0.5 to about 5 percent.

The concentration of alpha hydroxyacids used for stabilizing the dithranol composition may range from 0.01 to 1 percent by weight of the total composition. The preferred concentration range, however, is from 0.02 to about 0.5 percent.

The concentration of water used for dissolution of alpha hydroxyacids may range from 0.01 to 1 percent by volume of the total composition. The preferred concentration range, however, is from 0.02 to about 0.2 percent.

If desired, two or more of the aforementioned alpha hydroxyacids may be added as described above to form a stable dithranol composition of this invention. In this instance it is preferred that the concentration of the alpha hydroxyacids not exceed about 0.5 percent by weight of the total composition.

In preparing a water-in-oil emulsion the oil phase which contains a water-in-oil emulsifier and the aqueous phase are separately heated to 80° C., and the aqueous phase slowly poured into the melted oil phase with agitation. Agitation is continued until the mixture congeals. By changing the concentrations of water content and/or certain ingredients in the oil phase a cream or lotion type of water-in-oil emulsion may be readily obtained.

To prepare a stable dithranol composition in an anhydrous base such as petrolatum the alpha hydroxyacid stabilization agent may be dissolved in ethanol, and the alcoholic solution admixed with the base. In the alternative the stabilizing agent may be incorporated directly in the base in powder form. Dithranol is dissolved in acetone as described above, and is admixed then with the anhydrous base already containing the alpha hydroxyacid.

Stable dithranol compositions of the instant invention may also be prepared in a solution form. In this case dithranol is dissolved directly in a mixture of organic solvents containing alpha hydroxyacids. The organic solvents may include acetone, ethanol, propylene glycol, 1,3-butanediol, isopropyl myristate, isopropyl palmitate and mineral oil.

In our U.S. patent application entitled Therapeutic Compositions and Vehicles for Topical Pharmaceuticals Ser. No. 77,726 and filed on Sept. 21, 1979, a stable anhydrous vehicle is disclosed. This invention contemplates use of that vehicle also and the disclosure thereof is hereby incorporated by reference.

The following are illustrative examples for formulating dithranol compositions stabilized with alpha hydroxyacids of this invention. It should be understood that the examples are illustrative only and not limitative of the invention. Therefore, any of the aforementioned alpha hydroxyacids may be substituted according to the teachings of this invention in the following formulations.

EXAMPLE 1

A water-in-oil emulsion of pH 5.4 may be prepared as follows:

| Part A: | Sorbitan sesquioleate or sorbitan monooleate | 10 gm |
| --- | --- | --- |
| | Petrolatum | 15 gm |
| | Mineral oil | 15 gm |
| | Beeswax | 15 gm |
| | Isopropyl myristate or isopropyl palmitate | 10 gm |
| Part B: | Water | 23 ml |
| | Propylene glycol | 5 ml |
| | Glycerol | 3 ml |
| | Sorbitol | 3 ml |
| | Magnesium hydroxide or magnesium oxide | 0.1 gm |

Heat both Part A and Part B to 80° C. Add Part B slowly to Part A with agitation. After the mixture is congealed add 10% phosphoric acid 0.5 ml and aluminum chlorohydroxide 0.5 gm.

EXAMPLE 2

A therapeutic composition of pH 5.4 containing 0.01% dithranol stabilized with 0.1% citric acid in a water-in-oil emulsion may be prepared as follows:

Dithranol 0.01 gm is dissolved in 0.5 ml acetone and citric acid 0.1 gm is dissolved in 0.1 ml water. The acetone solution and the water solution thus prepared are admixed with 99 gm of the water-in-oil emulsion formulated according to Example 1. The mixing is continued until a uniform light yellowish cream is obtained.

EXAMPLE 3

A therapeutic composition of pH 4.1 containing 0.02% dithranol stabilized with 0.05% tartaric acid in a water-in-oil emulsion may be prepared as follows:

Dithranol 0.02 gm is dissolved in 1 ml acetone, and L-tartaric acid 0.05 gm is dissolved in 0.1 ml water. The acetone solution and the water solution thus prepared are admixed with 99 gm of the water-in-oil emulsion formulated according to Example 1. The mixing is continued until a uniform light yellowish cream is obtained.

EXAMPLE 4

A therapeutic composition of pH 4.2 containing 0.03% dithranol stabilized with 0.06% gluconolactone in a water-in-oil emulsion may be prepared as follows:

Dithranol 0.03 gm is dissolved in 1.5 ml acetone, and D-gluconolactone 0.06 gm is dissolved in 0.1 ml water. The acetone solution and the water solution thus prepared are admixed with 98 gm of the water-in-oil emulsion formulated according to Example 1. The mixing is continued until a uniform light yellowish cream is obtained.

EXAMPLE 5

A therapeutic composition of pH 3.8 containing 0.04% dithranol stabilized with 0.08% tartronic acid in a water-in-oil emulsion may be prepared as follows:

Dithranol 0.04 gm is dissolved in 2 ml acetone, and tartronic acid 0.08 gm is dissolved in 0.1 ml water. The acetone solution and the water solution thus prepared are admixed with 98 gm of the water-in-oil emulsion formulated according to Example 1. The mixing is continued until a uniform light yellowish cream is obtained.

EXAMPLE 6

A therapeutic composition of pH 4.4 containing 0.05% dithranol stabilized with 0.1% mucic acid in a water-in-oil emulsion may be prepared as follows:

Dithranol 0.05 gm is dissolved in 2.5 ml acetone, and mucic acid 0.1 gm is dissolved in 0.1 ml water. The acetone solution and the water solution thus prepared are admixed with 97 gm of the water-in-oil emulsion formulated according to Example 1. The mixing is continued until a uniform yellowish cream is obtained.

EXAMPLE 7

A therapeutic composition of pH 4.3 containing 0.05% dithranol stabilized with 0.2% citric acid in a water-in-oil emulsion may be prepared as follows:

Dithranol 0.05 gm is dissolved in 2.5 ml acetone, and citric acid 0.2 gm is dissolved in 0.2 ml water. The acetone solution and the water solution thus prepared are admixed with 97 gm of the water-in-oil emulsion formulated according to Example 1. The mixing is continued until a uniform light yellowish cream is obtained.

EXAMPLE 8

A therapeutic composition of pH 3.2 containing 0.06% dithranol stabilized with 0.1% malic acid in a water-in-oil emulsion may be prepared as follows:

Dithranol 0.06 gm is dissolved in 3 ml acetone, and DLmalic acid 0.1 gm is dissolved in 0.1 ml water. The acetone solution and the water solution thus prepared are admixed with 97 gm of the water-in-oil emulsion formulated according to Example 1. The mixing is continued until a uniform yellowish cream is obtained.

EXAMPLE 9

A therapeutic composition of pH 4.6 containing 0.07% dithranol stabilized with 0.1% glucoheptonolactone in a water-in-oil emulsion may be prepared as follows:

Dithranol 0.07 gm is dissolved in 3.5 ml acetone and D-glucoheptono-1.4-lactone 0.1 gm is dissolved in 0.2 ml water. The acetone solution and the water solution thus prepared are admixed with 96 gm of the water-in-oil emulsion formulated according to Example 1. The mixing is continued until a uniform yellowish cream is obtained.

EXAMPLE 10

A therapeutic composition of pH 3.8 containing 0.1% dithranol stabilized with 0.2% tartaric acid in a water-in-oil emulsion may be prepared as follows:

Dithranol 0.1 gm is dissolved in 5 ml acetone, and L-tartaric acid 0.2 gm is dissolved in 0.2 ml water. The acetone solution and the water solution thus prepared are admixed with 95 gm of the water-in-oil emulsion formulated according to Example 1. The mixing is continued until a uniform yellowish cream is obtained.

EXAMPLE 11

A therapeutic composition of pH 3.8 containing 0.1% dithranol stabilized with 0.2% citric acid in a water-in-oil emulsion may be prepared as follows:

Dithranol 0.1 gm is dissolved in 5 ml acetone, and citric acid 0.2 gm is dissolved in 0.2 ml water. The acetone solution and the water solution thus prepared are admixed with 95 gm of the water-in-oil emulsion formulated according to Example 1. The mixing is continued until a uniform yellowish cream is obtained.

EXAMPLE 12

A therapeutic composition of pH 3.9 containing 0.1% dithranol stabilized with 0.2% saccharic acid lactone in a water-in-oil emulsion may be prepared as follows:

Dithranol 0.1 gm is dissolved in 5 ml acetone, and D-saccharic acid-1, 4-lactone 0.2 gm is dissolved in 2 ml water. The acetone solution and the water solution thus prepared are admixed with 92 gm of the water-in-oil emulsion formulated according to Example 1. The mixing is continued until a uniform yellowish cream is obtained.

EXAMPLE 13

A therapeutic composition of pH 4.4 containing 0.1% dithranol stabilized with 0.4% saccharic acid monopotassium salt in a water-in-oil emulsion may be prepared as follows:

Dithranol 0.1 gm is dissolved in 5 ml acetone, and D-saccharic acid monopotassium salt 0.4 gm is dissolved in 2 ml water. The acetone solution and the water solution thus prepared are admixed with 93 gm of the water-in-oil emulsion formulated according to Example 1. The mixing is continued until a uniform yellowish cream is obtained.

EXAMPLE 14

A therapeutic composition of pH 4.8 containing 0.1% dithranol stabilized with 0.2% citric acid diammonium salt in a water-in-oil emulsion may be prepared as follows:

Dithranol 0.1 gm is dissolved in 5 ml acetone, and citric acid diammonium salt (also known as citric acid ammonium salt dibasic) 0.2 gm is dissolved in 0.4 ml water. The acetone solution and the water solution thus prepared are admixed with 94 gm of the water-in-oil emulsion formulated according to Example 1. The mixing is continued until a uniform yellowish cream is obtained.

EXAMPLE 15

A therapeutic composition of pH 2.4 containing 0.1% dithranol stabilized with 0.2% isocitric acid lactone in a water-in-oil emulsion may be prepared as follows:

Dithranol 0.1 gm is dissolved in 5 ml acetone, and isocitric acid lactone 0.2 gm is dissolved in 0.4 ml water. The acetone solution and the water solution thus prepared are admixed with 94 gm of the water-in-oil emulsion formulated according to Example 1. The mixing is continued until a uniform yellowish cream is obtained.

EXAMPLE 16

A therapeutic composition of pH 5.2 containing 0.1% dithranol stabilized with 0.2% galactonolactone in a water-in-oil emulsion may be prepared as follows:

Dithranol 0.1 gm is dissolved in 5 ml acetone, and galactonolactone 0.2 gm is dissolved in 0.4 ml water. The acetone solution and the water solution thus prepared are admixed with 94 gm of the water-in-oil emulsion formulated according to Example 1. The mixing is continued until a uniform yellowish cream is obtained.

EXAMPLE 17

A therapeutic composition of pH 3.4 containing 0.1% dithranol stabilized with 0.2% glucuronic acid in a water-in-oil emulsion may be prepared as follows:

Dithranol 0.1 gm is dissolved in 5 ml acetone, and D-glucuronic acid 0.2 gm is dissolved in 0.4 ml water. The acetone solution and the water solution thus prepared are admixed with 94 gm of the water-in-oil emulsion formulated according to Example 1. The mixing is continued until a uniform yellowish cream is obtained.

EXAMPLE 18

A therapeutic composition of pH 5.3 containing 0.1% dithranol stabilized with 0.2% glucuronamide in a water-in-oil emulsion may be prepared as follows:

Dithranol 0.1 gm is dissolved in 5 ml acetone and glucuronamide 0.2 gm is dissolved in 0.4 ml water. The acetone solution and the water solution thus prepared are admixed with 94 gm of the water-in-oil emulsion formulated according to Example 1. The mixing is continued until a uniform yellowish cream is obtained.

EXAMPLE 19

A therapeutic composition of pH 3.6 containing 0.1% dithranol stabilized with 0.2% galacturonic acid in a water-in-oil emulsion may be prepared as follows:

Dithranol 0.1 gm is dissolved in 5 ml acetone, and α-D-galacturonic acid 0.2 gm is dissolved in 0.4 ml water. The acetone solution and the water solution thus prepared are admixed with 94 gm of the water-in-oil emulsion formulated according to Example 1. The mixing is continued until a uniform yellowish cream is obtained.

EXAMPLE 20

A therapeutic composition of pH 3.2 containing 0.1% dithranol stabilized with 0.25% glyceric acid in a water-in-oil emulsion may be prepared as follows:

Glyceric acid (65% aqueous solution) 0.38 ml and a solution prepared from dithranol 0.1 gm in 5 ml acetone are admixed with 95 gm of the water-in-oil emulsion formulated according to Example 1. The mixing is continued until a uniform yellowish cream is obtained.

EXAMPLE 21

A therapeutic composition of pH 4.8 containing 0.01% dithranol stabilized with 0.02% tartaric acid in a petrolatum base may be prepared as follows:

Dithranol 0.01 gm is dissolved in 0.5 ml acetone, and L-tartaric acid 0.02 gm is dissolved in 0.5 ml ethanol. The acetone solution and the ethanol solution thus prepared are admixed with a base made of 60 gm petrolatum USP and 40 gm mineral oil USP. The mixing is continued until a uniform light yellowish ointment is obtained.

EXAMPLE 22

A therapeutic composition of ph 3.0 containing 0.02% dithranol stabilized with 0.1% tartaric acid in a petrolatum base may be prepared as follows:

Dithranol 0.02 gm is dissolved in 1 ml acetone, and L-tartaric acid 0.1 gm is dissolved in 2 ml ethanol. The acetone solution and the ethanol solution thus prepared are admixed with a base made of 60 gm petrolatum USP and 37 gm mineral oil USP. The mixing is continued until a uniform light yellowish ointment is obtained.

EXAMPLE 23

A therapeutic composition of pH 3.6 containing 0.03% dithranol stabilized with 0.1 citric acid in a petrolatum base may be prepared as follows:

Dithranol 0.03 gm is dissolved in 1.5 ml acetone, and citric acid 0.1 gm is dissolved in 2 ml ethanol. The acetone solution and the ethanol solution thus prepared are admixed with a base made of 5 gm spermaceti, 5 gm beeswax, 10 gm isopropyl myristate, 50 gm petrolatum and 26 gm mineral oil. The mixing is continued until a uniform yellowish ointment is obtained.

EXAMPLE 24

A therapeutic composition of pH 2.4 containing 0.05% dithranol stabilized with 0.2% tartaric acid in a petrolatum base may be prepared as follows:

Dithranol 0.05 gm is dissolved in 2.5 ml acetone, and L-tartartic acid 0.2 gm is dissolved in 4 ml ethanol. The acetone solution and the ethanol solution thus prepared are admixed with a base made of 60 gm petrolatum USP and 33 gm mineral oil USP. The mixing is continued until a uniform yellowish ointment is obtained.

EXAMPLE 25

A therapeutic composition of pH 2.0 containing 0.05% dithranol stabilized with 0.2% citric acid in a petrolatum base may be prepared as follows:

Dithranol 0.05 gm is dissolved in 2.5 ml acetone and citric acid 0.2 gm is dissolved in 4 ml ethanol. The acetone solution and the ethanol solution thus prepared are admixed with a base made of 5 gm spermaceti, 5 gm beeswax, 10 gm isopropyl palmitate, 50 gm petrolatum and 23 gm mineral oil. The mixing is continued until a uniform yellowish ointment is obtained.

EXAMPLE 26

A therapeutic composition of pH 4.0 containing 0.02% dithranol stabilized with 0.1% tartronic acid in a nonaqueous base may be prepared as follows:

Dithranol 0.02 gm is dissolved in 1 ml acetone, and tartronic acid 0.1 gm is dissolved in 3 ml ethanol. The acetone solution and the ethanol solution thus prepared are admixed with a base of 10 gm beeswax, 70 gm isopropyl myristate, 10 gm petrolatum and 6 gm mineral oil. The mixing is continued until a uniform light yellowish ointment is obtained.

EXAMPLE 27

A therapeutic composition of pH 3.6 containing 0.04% dithranol stabilized with 0.1% tartronic acid in a nonaqueous base may be prepared as follows:

Dithranol 0.04 gm is dissolved in 2 ml acetone, and tartronic acid 0.1 gm is dissolved in 3 ml ethanol. The acetone solution and the ethanol solution thus prepared are admixed with a base made of 10 gm beeswax, 70 gm isopropyl palmitate, 10 gm petrolatum and 5 gm mineral oil. The mixing is continued until a uniform yellowish ointment is obtained.

EXAMPLE 28

A therapeutic composition of pH 4.6 containing 0.01% dithranol stabilized with 0.05% citric acid in an anhydrous base may be prepared as follows:

Dithranol 0.01 gm is dissolved in 0.5 ml acetone, and citric acid 0.05 gm is dissolved in 1 ml ethanol. The acetone solution and the ethanol solution thus prepared are admixed with a base made of 10 gm spermaceti, 70 gm isopropyl myristate, 10 gm petrolatum and 8 gm mineral oil. The mixing is continued until a uniform light yellowish ointment is obtained.

EXAMPLE 29

A therapeutic composition of pH 4.4 containing 0.03% dithranol stabilized with 0.1% citric acid in an anhydrous base may be prepared as follows:

Dithranol 0.03 gm is dissolved in 1.5 ml acetone and citric acid 0.1 gm is dissolved in 2 ml ethanol. The acetone solution and the ethanol solution thus prepared are admixed with a base made of 10 gm spermaceti, 70 gm isopropyl palmitate, 10 gm petrolatum and 6 gm mineral oil.

EXAMPLE 30

A therapeutic composition of pH 4.6 containing 0.01% dithranol stabilized with 0.05% tartaric acid in a solution form may be prepared as follows:

Dithranol 0.01 gm and L-tartaric acid 0.05 gm are directly dissolved in a solution made of 90 ml ethanol and 10 ml propylene glycol. This therapeutic solution may be stored in 2 ounce dropper bottles suitable for topical application to hairy skin areas such as the scalp.

EXAMPLE 31

A therapeutic composition of pH 4.2 containing 0.02% dithranol stabilized with 0.06% tartaric acid in a solution form may be prepared as follows:

Dithranol 0.02 gm and L-tartaric acid 0.06 gm are directly dissolved in a solution made of 80 ml ethanol and 20 ml propylene glycol.

EXAMPLE 32

A therapeutic composition of pH 4.1 containing 0.04% dithranol stabilized with 0.08% tartaric acid in a solution form may be prepared as follows:

Dithranol 0.04 gm and L-tartaric acid 0.08 gm are directly dissolved in a solution made of 2 ml acetone, 78 ml ethanol and 20 ml propylene glycol.

EXAMPLE 33

A therapeutic composition of pH 4.3 containing 0.03% dithranol stabilized with 0.3% citric acid in an anhydrous base may be prepared as follows:

Glyceryl monostearate 20 gm flake form, mineral oil 10 gm and isopropyl myristate or isopropyl palmitate 70 gm are heated to about 65° C. until the mixture is completely melted. Dithranol 0.03 gm and citric acid 0.3 gm are added to the melt with agitation. Continue agitation during the cooling process until the mixture is congealed to a light yellowish cream.

EXAMPLE 34

A therapeutic composition of pH 4.1 containing 0.03% dithranol stabilized with 0.3% tartronic acid in an anhydrous base may be prepared as follows:

Glyceryl monostearate 20 gm flake form, mineral oil 10 gm and isopropyl myristate or isopropyl palmitate 70 gm are heated to about 65° C. until the mixture is completely melted. Dithranol 0.03 gm and tartronic acid 0.3 gm are added to the melt with agitation. Continue agitation during the cooling process until the mixture is congealed to a yellowish cream.

EXAMPLE 35

A therapeutic composition of pH 4.5 containing 0.03% dithranol stabilized with 0.3% tartaric acid in an anhydrous base may be prepared as follows:

Glyceryl monostearate 20 gm flake form, mineral oil 10 gm and isopropyl myristate or isopropyl palmitate 70 gm are heated to about 65° C. until the mixture is completely melted. Dithranol 0.03 gm and tartaric acid 0.3 gm are added to the melt with agitation. Continue agitation during the cooling process until the mixture is congealed to a yellowish cream.

EXAMPLE 36

A therapeutic composition of pH 5.8 containing 0.03% dithranol stabilized with 0.3% tartaric acid in an anhydrous base may be prepared as follows:

Glyceryl monostearate 15 gm flake form, mineral oil 25 gm and isopropyl myristate or isopropyl palmitate 60 gm are heated to about 65° C. until the mixture is completely melted. Dithranol 0.03 gm and tartaric acid 0.3 gm are added to the melt with agitation. Continue agitation during the cooling process until the mixture is congealed to a yellowish cream.

TEST RESULTS (A) Chemical Stability

When dithranol is freshly prepared in a solution, a cream, an ointment or a paste the composition shows a bright yellowish color. Without addition of any stabilizers the composition which contains dithranol will change in color from yellow to brown at room temperature in a matter of a few days to a few weeks depending on whether the composition contains water or not. For example, dithranol 0.05% in hydrophilic ointment USP changed in color from yellow to gray within 24 hours at room temperature, and the cream turns to a brown color within 48 hours. Under the same conditions, dithranol 0.05% in petrolatum base changes in color slowly from bright yellow to grayish yellow within 24 hours at room temperature, and the ointment turns into a brown color after 12 days.

It has been shown that a dithranol composition is therapeutically efficacious as long as the composition does not change in color from yellowish to brownish. Therefore, the simplest method to ascertain whether a substance is a dithranol stabilizer or not is to determine whether the yellowish color of the composition is prolonged.

In order to determine the dithranol stabilizing effect of the present invention all test substances at various concentrations were incorporated into the compositions containing dithranol prepared according to Examples. Each test composition was stored in a two ounce glass jar and it was left at room temperature for an extended period of time.

A test substance is determined to be a dithranol stabilizer when a water-containing dithranol composition which also contains the test substance does not change yellowish color at room temperature for more than one month. Generally, the concentrations of dithranol and a test substance in the composition were 0.1% and 0.2% respectively. Water-in-oil emulsions were used as vehicles in most instances. More than 50 chemical substances have been tested for their potential stabilizing effect on dithranol. Chemical substances which we have found so far to be dithranol stabilizers are collectively known as alpha hydroxyacids. The alpha hydroxyacids which we have tested and which we have discovered to be dithranol stabilizers are of two classes and are listed below.

| (I) Glyceric acid derivatives | |
|---|---|
| 1. Glyceric acid | 6. Galactonic acid |
| 2. Gluconic acid | 7. Galactonolactone |
| 3. Gluconolactone | 8. Glucuronic acid |
| 4. Glucoheptonic acid | 9. Glucuronolactone |
| 5. Glucoheptonolactone | 10. Galacturonic acid |
| | 11. Glucuronamide |
| (II) Alpha hydroxy polycarboxylic acids | |
| 1. Tartronic acid | 6. Citric acid ammonium salt |
| 2. Malic acid | 7. Saccharic acid |
| 3. Tartaric acid | 8. Saccharic acid monopotassium salt |
| 4. Citric acid | 9. Saccharic acid lactone |
| 5. Isocitric acid lactone | 10. Mucic acid |

Under our test conditions the following compounds have been found to be partially effective; i.e., only stabilized for two weeks.

1. Lactic acid
2. Glycolic acid
3. Salicylic acid
4. Stannous chloride
5. Sodium bisulfite
6. Sodium metabisulfite
7. Citric acid tripotassium salt unacidified
8. Citric acid trisodium salt unacidified
9. Ascorbic acid (B) Clinical test The involved skin in psoriasis is hyperplastic (thickened), erythematous (red or inflamed), and has thick adherent scales. The degree of thickening is such that lesions are elevated up to 1 mm above the surface of adjacent normal skin; erythema is usually an intense red; the thickened adherent scales cause the surface of involved skin to be markedly rough and uneven. These three attributes of thickness, color and texture can be quantified to allow objective measurement of degree of improvement from topically applied therapeutic test materials as follows:

|  | Degree of Improvement | | | | |
| --- | --- | --- | --- | --- | --- |
|  | None (0) | Mid (1+) | Moderate (2+) | Substantial (3+) | Complete (4+) |
| Thickness | Highly elevated | Detectable reduction | Readily apparent | Barely elevated | Normal thickness |
| Texture | Visibly rough | Palpably rough | Uneven but not rough | Slightly uneven | Visibly and palpably smooth |
| Color | Intense red | Red | Dark pink | Light pink | Normal skin color |

In order to ascertain whether the dithranol compositions stabilized with alpha hydroxyacids are therapeutically efficacious for topical treatment of psoriasis, a total of more than 24 patients having psoriasis were treated in this study.

Therapeutic compositions of dithranol stabilized with alpha hydroxyacids were prepared according to the Examples. Treatment areas in patients having psoriasis were localized lesions 4-15 cm in diameter. The medicinal creams or ointments were topically applies by the patient in an amount sufficient to cover the treatment site. Applications were made two-three times daily and without occlusive dressings. Clinical evaluations of degrees of improvement were made at weekly or biweekly intervals. Treatment periods generally lasted for six weeks, unless clearing of disease occurred earlier and an evaluation of degree improvement was made at that time. The treatment results on psoriatic patients are summarized on the following table.

TABLE 1

Effects[a] on Psoriasis of Topical Dithranol Compositions Stabilized with Glyceric Acid Derivatives

| Stabilizer | Stabilizer Concentration % | Dithranol Concentration % | Number of Patients | Average Therapeutic Efficacy |
| --- | --- | --- | --- | --- |
| Gluconolactone | 0.1 | 0.05 | 19 | 3+ |
|  | 0.2 | 0.1 | 21 | 4+ |
| Galactonolactone | 0.1 | 0.05 | 16 | 3+ |
|  | 0.2 | 0.1 | 17 | 3+ |
| Glucuronic acid | 0.1 | 0.02 | 9 | 2+ |
|  | 0.2 | 0.1 | 11 | 3+ |
| Glucuronamide | 0.1 | 0.05 | 18 | 2+ |
|  | 0.2 | 0.1 | 17 | 3+ |
| Galacturonic acid | 0.1 | 0.05 | 19 | 3+ |
|  | 0.2 | 0.1 | 19 | 4+ |
| Glucoheptonolactone | 0.2 | 0.1 | 13 | 3+ |
| Glyceric acid | 0.2 | 0.1 | 14 | 4+ |

[a]The clinical evaluations were made at the end of six week topical application.

As shown by the above Table 1, all seven therapeutic compositions containing 0.1% dithranol stabilized with 0.2% glyceric acid or its derivative caused substantial or complete improvements in the patients tested. At a lower concentration (0.05%) of dithranol the compositions caused moderate to substantial improvement of psoriatic lesions in the patients tested.

TABLE 2

Effects[a] on Psoriasis of Topical Dithranol Compositions Stabilized with Alpha Hydroxy Polycarboxylic Acids

| Stabilizer | Stabilizer Concentration % | Dithranol Concentration % | Number of Patients | Average Therapeutic Efficacy |
| --- | --- | --- | --- | --- |
| Malic acid | 0.1 | 0.05 | 15 | 3+ |
|  | 0.2 | 0.1 | 15 | 3+ |
| Tartronic acid | 0.1 | 0.05 | 14 | 2+ |
|  | 0.2 | 0.1 | 14 | 4+ |
| Tartaric acid | 0.1 | 0.05 | 11 | 3+ |
|  | 0.2 | 0.1 | 12 | 4+ |
| Citric acid | 0.1 | 0.02 | 18 | 3+ |
|  | 0.1 | 0.05 | 18 | 4+ |
| Citric acid Ammonium Salt | 0.1 | 0.05 | 13 | 2+ |
|  | 0.2 | 0.1 | 13 | 3+ |
| Saccharic acid | 0.1 | 0.05 | 14 | 2+ |
| Lactone | 0.2 | 0.1 | 14 | 3+ |
| Mucic acid | 0.1 | 0.05 | 17 | 2+ |
|  | 0.2 | 0.1 | 15 | 3+ |

[a]The clinical evaluations were made at the end of six weeks of topical application.

As exhibited by the above Table 2 three compositions containing 0.1% dithranol stabilized with 0.2% each of tartronic acid, tartaric acid or citric acid achieved complete clearing of psoriasis, restoring the involved skin to a state of normal appearance, normal thickness, and visibly and palpably smooth in the patients tested. The rest of the compositions achieved improvements of from moderate to substantial degree in the patients tested.

In order to determine whether the dithranol compositions stabilized with alpha hydroxyacids are therapeutically efficacious for topical treatment of eczema and seborrheic dermatitis, a total of five patients having eczema and four patients having seborrheic dermatitis were tested in another study.

Therapeutic compositions in solution, lotion, water-in-oil emulsion or nonaqueous ointment form of dithranol stabilized with alpha hydroxyacids were prepared according to the Examples. Conditions and schedules for treatment of eczema were the same as that of psoriasis. For treatment of seborrheic dermatitis a solution or a lotion form of therapeutic compositions is preferred because of their use in the hairy skin area such as the scalp. Patients having seborrheic dermatitis on the scalp were instructed to apply topically the dithranol solution or lotion stabilized with alpha hydroxyacids. Applications were made one or two times daily and without any kind of additional treatment. The same therapeutic compositions may also be used for topical treatment of psoriatic patients having scalp involvement.

The test results on patients having eczema and patients having seborrheic dermatitis on the scalp are summarized in the following tables.

TABLE 3

Effects on Eczema of Topical Dithranol Compositions Stabilized with Alpha Hydroxyacids

| Stabilizer | Stabilizer Concentration (%) | Dithranol Concentration (%) | Number of Patients | Average Therapeutic Efficacy |
|---|---|---|---|---|
| Gluconolactone | 0.2 | 0.1 | 5 | 3+ |
| Tartaric Acid | 0.2 | 0.1 | 4 | 4+ |

<sup>a</sup>The clinical evaluations were made at the end of six weeks topical application.

TABLE 4

Effects<sup>a</sup> on Scalp Seborrheic Dermatitis by Topical Dithranol Compositions Stabilized with Alpha Hydroxyacids

| Stabilizer | Stabilizer Concentration (%) | Dithranol Concentration (%) | Number of Patients | Average Therapeutic Efficacy |
|---|---|---|---|---|
| Citric Acid | 0.2 | 0.05 | 4 | 4+ |
| Galacturonic Acid | 0.2 | 0.05 | 4 | 3+ |

<sup>a</sup>The clinical evaluations were made at the end of six weeks topical application.

As shown by the above Table 3 and Table 4, all four therapeutic compositions containing 0.1% or 0.05% dithranol stabilized with 0.02% gluconolactone, tartaric acid, citric acid or galacturonic acid caused substantial or complete improvements in the patients treated.

The invention may be embodied in other specific forms without departing from the spirit or essential characteristics thereof. The present embodiments are therefore to be considered in all respects as illustrative and not restrictive, the scope of the invention being indicated by the appended claims, and all changes are, therefore, intended to be embraced herein.

What is claimed:

1. In a composition containing a anti-inflammatory effective amount of dithranol in a pharmaceutically acceptable vehicle for topical application, the improvement comprising: a stabilizing effective amount of at least one member selected from the group consisting of: a glyceric acid or a derivative thereof having the formula $$R(CR_1OH)_n COOH$$

wherein
n=2,3,4,5,6, or 7 and
$R, R_1$=H, CHO, or alkyl having from 1 to 7 carbon atoms, or the lactone or amide thereof; and an alpha hydroxy polycarboxylic or a derivative thereof having the formula $$(CRX)_m (COOH)_n$$

wherein
m=1,2,3,4,5, or 6
n=2,3,4 and
X=OH or H when m≥2 and with one or more than one OH group present.
R=H, CHO, or alkyl having from 1 to 7 carbon atoms, or the lactone, amide or salt thereof.

2. The composition of claim 1 wherein said member is a compound selected from the group consisting of:

| Glyceric acid | Galatonolactone |
|---|---|
| Gluconic acid | Glucuronic acid |
| Glucoheptonic acid | Glucuronolactone |
| Glucoheptonolactone | Galacturonic acid |
| Galactonic acid | Galacturonolactone, and |
| Gluconolactone | Glucuronamide |

3. The composition of claim 1 wherein said member is a compound selected from the group consisting of:

| Tartronic acid | Mucic acid lactone |
|---|---|
| Malic acid | Saccharic acid monopotassium salt |
| Tartaric acid | Saccharic acid monosodium salt |
| Citric acid | Saccharic acid monoammonium salt |
| Isocitric acid | Tartaric acid monoamide |
| Saccharic acid | Citric acid diamide |
| Mucic acid | Tartaric acid monoethyl ester, and |
| Saccharic acid lactone | Isocitric acid lactone |

4. The composition of claim 1 wherein dithranol is present in a concentration of from 0.01 to 0.5 percent, by weight of the total composition.

5. The composition of claim 4 wherein the concentration of dithranol is no more than 0.1 percent, by weight.

6. The composition of claim 1 wherein the member is present in a concentration of 0.01 to 1 percent by weight of the total composition.

7. The composition of claim 6 wherein said member is present in a concentration of from 0.02 to 0.5 percent.

8. The composition of claim 1 wherein said vehicle is anhydrous.

9. The composition of claim 1 wherein said vehicle is a water-in-oil emulsion.

10. A method for stabilizing a dithranol containing composition wherein an anti-inflammatory effective amount of dithranol is admixed with a pharmaceutically acceptable vehicle for topical application to predetermined areas of the human body comprising:
admixing in said composition a chemical stabilizing effective amount against oxidation in air and water of at least one member selected from the group consisting of: glyceric acid or a derivative thereof having the formula $$R(CR_1OH)_n COOH$$

wherein
n=2,3,4,5,6 or 7, and
$R, R_1$=H, CHO, or alkyl having from 1 to 7 carbon atoms, or the lactone or amide thereof; and an alphahydroxy polycarboxylic acid or a derivative thereof having the formula $$(CRX)_m(COOH)_n$$

wherein
m=1,2,3,4,5, or 6
n=2,3,4, and
X=OH or H when m≥2 and with at least one OH group present
R=H, CHO, or alkyl having from 1 to 7 carbon atoms, or the lactone amide or salt thereof.

11. The method of claim 10 wherein said member is a compound selected from the group consisting of

| Glyceric acid | Glucuronic acid |
|---|---|
| Gluconic acid | Glucuronolactone |
| Gluconolactone | Galacturonic acid |
| Glucoheptonic acid | Galacturonolactone acid |
| Glucoheptonolactone | Glucuronamide |

-continued

Galactonic acid
Galactonolactone

12. The method of claim 10 wherein said member is a compound selected from the group consisting of

| | |
|---|---|
| Tartronic acid | Mucic acid lactone |
| Malic acid | Saccharic acid monopotassium salt |
| Tartaric acid | Saccharic acid monosodium salt |
| Citric acid | Saccharic acid monoammonium salt |
| Isocitric acid | Tartaric acid monoamide |
| Saccharic acid | Citric acid diamide |
| Mucic acid | Tartaric acid monoethyl ester, and |
| Saccharic acid lactone | Isocitric acid lactone |

13. The method of claim 10 wherein said member is present in a concentration of from 0.01 to 1 percent by weight of the total composition.

14. The method of claim 13 wherein said member is present in a concentration of from 0.02 to 0.5 percent.

15. The method of claim 10 wherein said member is initially dissolved in a solvent selected from the group consisting of water and alcohol and the solution admixed with said vehicle for incorporation into said composition.

16. The method of claim 10 wherein dithranol is dissolved in a solvent selected from the group consisting of acetone, ethanol, propylene glycol, 1-3 butanediol, isopropyl myristate, isopropyl palmitate and mineral oil and the solution admixed with said vehicle.

17. The method of claim 10 wherein dithranol is present in a concentration of 0.01 to 0.5 percent by weight of the total composition.

18. The method of claim 17 wherein dithranol is present in a concentration of from 0.01 to 0.1 percent by weight.

19. The method of claim 16 wherein said solvent is present in a concentration of from 0.5 to about 25 percent by volume of the total composition.

20. The method of claim 19 wherein said solvent is present in from 0.5 to about 5 percent.

21. The method of claim 15 wherein said solvent is water present in from 0.01 to 1 percent by volume of the total composition.

22. The method of claim 21 wherein water is present in a concentration of 0.02 to 0.2 percent.

23. The method of claim 10 wherein said vehicle is anhydrous.

24. The method of claim 10 wherein said vehicle is a water-in-oil emulsion.

* * * * *